United States Patent [19]

Koch

[11] Patent Number: 4,956,530
[45] Date of Patent: Sep. 11, 1990

[54] METHOD OF OPERATION AND DEVICE FOR EVEN HEATING BY MEANS OF MICROWAVES

[75] Inventor: Klaus Koch, Laatzen, Fed. Rep. of Germany

[73] Assignee: Hermann Berstorff Maschinenbau GmbH, Hanover, Fed. Rep. of Germany

[21] Appl. No.: 404,644

[22] Filed: Sep. 8, 1989

[30] Foreign Application Priority Data

Sep. 10, 1988 [DE] Fed. Rep. of Germany ....... 3830867

[51] Int. Cl.$^5$ .......................... H05B 6/68; H05B 6/78
[52] U.S. Cl. ...................... 219/10.55 B; 219/10.55 A; 219/10.55 M; 99/325; 364/477; 426/234
[58] Field of Search ................. 219/10.55 B, 10.55 A, 219/10.55 E, 10.55 M, 10.55 R, 518, 388; 99/DIG. 14, 451, 325, 443 C; 426/234, 241, 243; 364/477; 340/686, 687; 432/43, 122, 124; 414/161, 273, 274

[56] References Cited

U.S. PATENT DOCUMENTS

| | | | |
|---|---|---|---|
| 3,559,820 | 2/1971 | Munson | 340/686 |
| 3,699,899 | 10/1972 | Schiffmann et al. | 219/10.55 A |
| 3,745,307 | 7/1973 | Peek, Jr. et al. | 219/388 |
| 4,004,138 | 1/1977 | Morooka et al. | 364/477 X |
| 4,554,437 | 11/1985 | Wagner et al. | 219/388 |
| 4,659,892 | 4/1987 | Hammond et al. | 219/10.57 |
| 4,688,180 | 8/1987 | Motomiya | 364/477 |
| 4,808,782 | 2/1989 | Nakagawa et al. | 219/10.55 M |
| 4,839,485 | 6/1989 | Koch et al. | 219/10.55 A |

Primary Examiner—Philip H. Leung
Attorney, Agent, or Firm—Foley & Lardner, Schwartz, Jeffery, Schwaab, Mack, Blumenthal & Evans

[57] ABSTRACT

A method and apparatus for even and rapid heating, pasteurization or sterilization of food by microwave energy. The products to be heated are passed through an oblong microwave treatment chamber on a continuous conveyor belt. The beginning and end of a container on the conveyor is registered before or during entry into the treatment chamber, and this information is transmitted to a computer. On the basis of this information, the computer switches on and off the input microwave energy of the individual input channels when the containers or packages pass under the input channels, the switch-on and switch-off points being set in relation to the container or package length and the axial aperture center of the input channels. The microwave energy to be input into the product is preset in the computer.

10 Claims, 3 Drawing Sheets

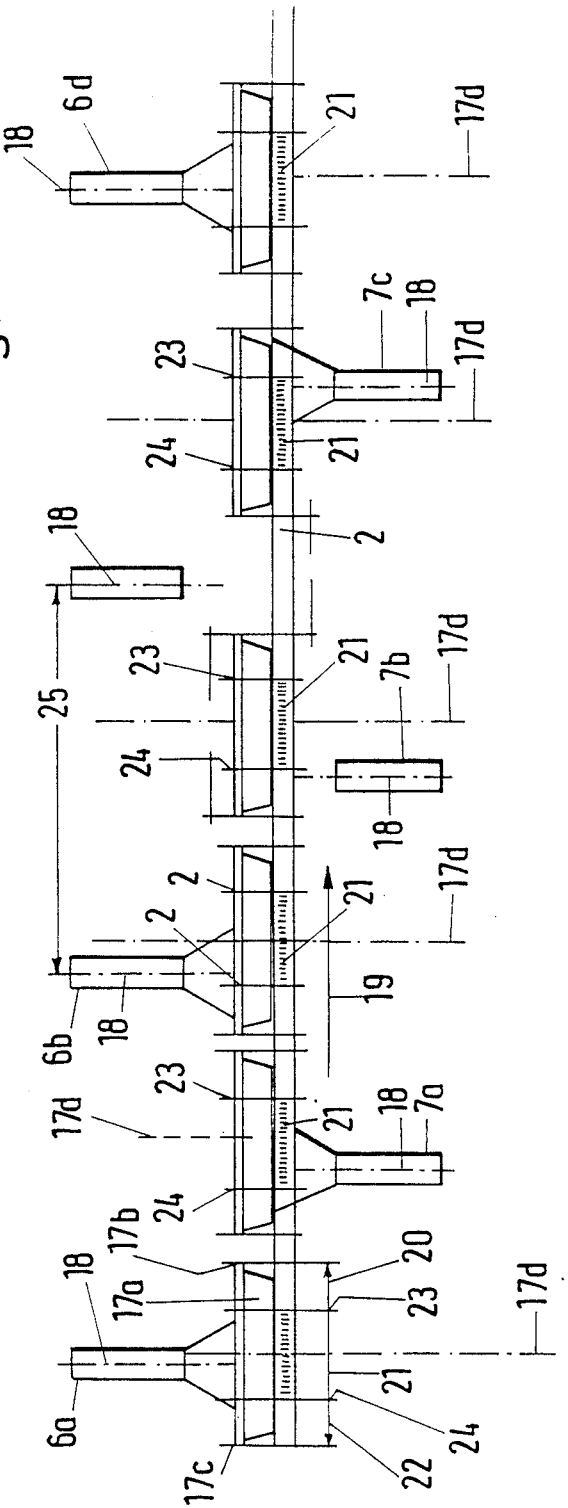

METHOD OF OPERATION AND DEVICE FOR EVEN HEATING BY MEANS OF MICROWAVES

BACKGROUND OF THE INVENTION

The invention relates to a method and apparatus for the even heating of containers by means of microwaves.

A device for pasteurizing by means of microwaves is known from German Patent 3,447,544. It has an oblong microwave treatment chamber with a continuous conveyor belt running through the chamber. The treatment chamber has microwave input channels.

This device requires exact uniform non-metallic transport containers for the goods, which must be positioned exactly on the conveyor belt. Slight deviations from the envisaged positions in the conveying direction on the continuous conveyor belt lead to a displacement of the entire microwave input operation, as a result of which local burnings become unavoidable.

SUMMARY OF THE INVENTION

The object of the invention is to provide a method of operation with which it is possible to implement a very even heating of products stored in open containers, for example chemical and pharmaceutical products, or ready meals, for the purpose of carrying out a pasteurization operation. A particular objective is that in arranging the containers or packages on the conveyor belt, the package length as well as the distances between them can be freely selected. It is thus possible to adapt the system to a wide range of products with respect to the treatment intensity and duration without great effort.

By virtue of the systematic recording or registration of the beginning and end of the containers on the conveyor belt before entry into the system, it is possible to carry out a dosed microwave energy input into each container, without it being necessary to take account of an exact positioning of the packages relative to one another, and the intervening distances in the conveying direction. In daily operation of a system of this type, this advantage is of decisive importance.

However, the method according to the invention also affords considerable advantages with respect to energy saving. The energy required to reach a predetermined product temperature is only fed to the product in a container or the packaged product when it is below an aperture of the microwave input channels. As a result of switching off the microwave input when there is no container below the input aperture, a great deal of energy is saved.

The greatest advantage of the method of operation is, however, that it is possible to maintain a specific cycle length or a cycle time with respect to each individual package, in order to ensure a uniform temperature distribution in the packages.

The registration of the containers before they enter the treatment chamber offers considerable advantages. There is no need to arrange position pickups to be connected to a control unit at the respective input channels in the treatment chamber.

The arrangement of such position pickups including their cabling in the treatment chamber, which has a high temperature (e.g. 150° C.), is very problematical. Because of the high temperature in the treatment chamber, position pickups and their cabling have only a very short service life. Malfunctions in the energy input and fires in the treatment chamber are the consequence. Moreover, a sensor design which is not impaired or destroyed by the electrical fields of the microwave generators is necessary.

The selection of the switch-on and switch-off point, or the setting in relation of the switch-on and switch-off point to the container length and to the aperture center of the input channels, permits a very individual adoption of the switching on and off of the microwave input. In this manner, the widest variety of package lengths and heating times can be set. It is also possible to determine individually the intensity of the microwave treatment (level of microwave energy). If the switch-on point is selected to be too early, that is before the package runs under the input channel, local overheating arises at the beginning of the packages. If the switch-on point is selected to be too late, the beginning of the package on the conveyor belt is heated too little. The result of this is an uneven heating.

The energy output can be stopped before the end of the package is vertically under the exit aperture of the input channel, depending on the length and the contents of the package.

The length of the container to be treated is fed into the computer. In this case, however, only packages of identical length can be treated, but without the necessity of the distances between them being identical.

The invention also provide a method of operation which permits the treatment of containers of different length because both the beginning and the end is recorded, for example by a sensor device, and the input microwave energy is correspondingly controlled. By exactly defining the switch-on and switch-off point, it is possible to set an even heating of the beginning and end of the packages regardless of the container length.

The microwave energy, which is input between the switch-on and switch-off point into the containers or packages, can be input intermittently, during the transport of the container under the exit aperture of the input channels. The input cycle length can be selected, for example, to be the same as the switch-off pulse of the microwave input. The intermittent microwave input is carried out until the switch-off point is reached. The intermittent input has the advantage of obtaining a better temperature evenness. However, in particular, the surface of the product to be treated is not subject to any overheating and hence damage.

A further possibility of improving the temperature evenness is achieved if the microwave input is controlled specifically with respect to the energy level between the switch-on and switch-off point, for example if 600 watts equal to 50% is used at the beginning and an increase to 100%, that is to 1.2 KW, takes place in the middle of the container or of the package. The energy is then reduced again to 600 watts at the end of the package.

The control of the form of the energy of the microwave input also leads to a further evening out of the temperature. The form of the energy can be selected to be rectangular, trapezoidal, triangular or sinusoidal, in each case depending on the surface form of the product in the container or in the package. The surface of the product should under no circumstances be subjected for too long to excessively high microwave energy, because, for example, with too high an energy input into products with an already elevated temperature ($T = 70°$ C), a liquid surface (meat with gravy) enters the steam phase and consequently can cause the package to burst.

A heterogeneous surface (for example cauliflower) is a larger surface and hence permits a better energy distribution in the product. The microwave energy in this case reaches further into the product and can thus be distributed better (lesser energy density).

The form of the energy is advantageously designed in such a way that as the product surface temperature increases, the energy peak acts more and more briefly on the product surface (sequence: rectangular, trapezoidal, sinusoidal, triangular). The selection of the respective energy form is therefore made depending on the temperature development in the product, especially, however, with respect to temperature development of the surface of the product.

BRIEF DESCRIPTION OF THE DRAWINGS

Preferred exemplary embodiments of the invention will be described below with reference to the drawings, in which:

FIG. 2 diagrammatically illustrates the process of energy input;

FIG. 3 shows a representation of the temperature distribution in a package;

DETAILED DESCRIPTION OF THE PREFERRED EMBODIMENTS

Figure 1:
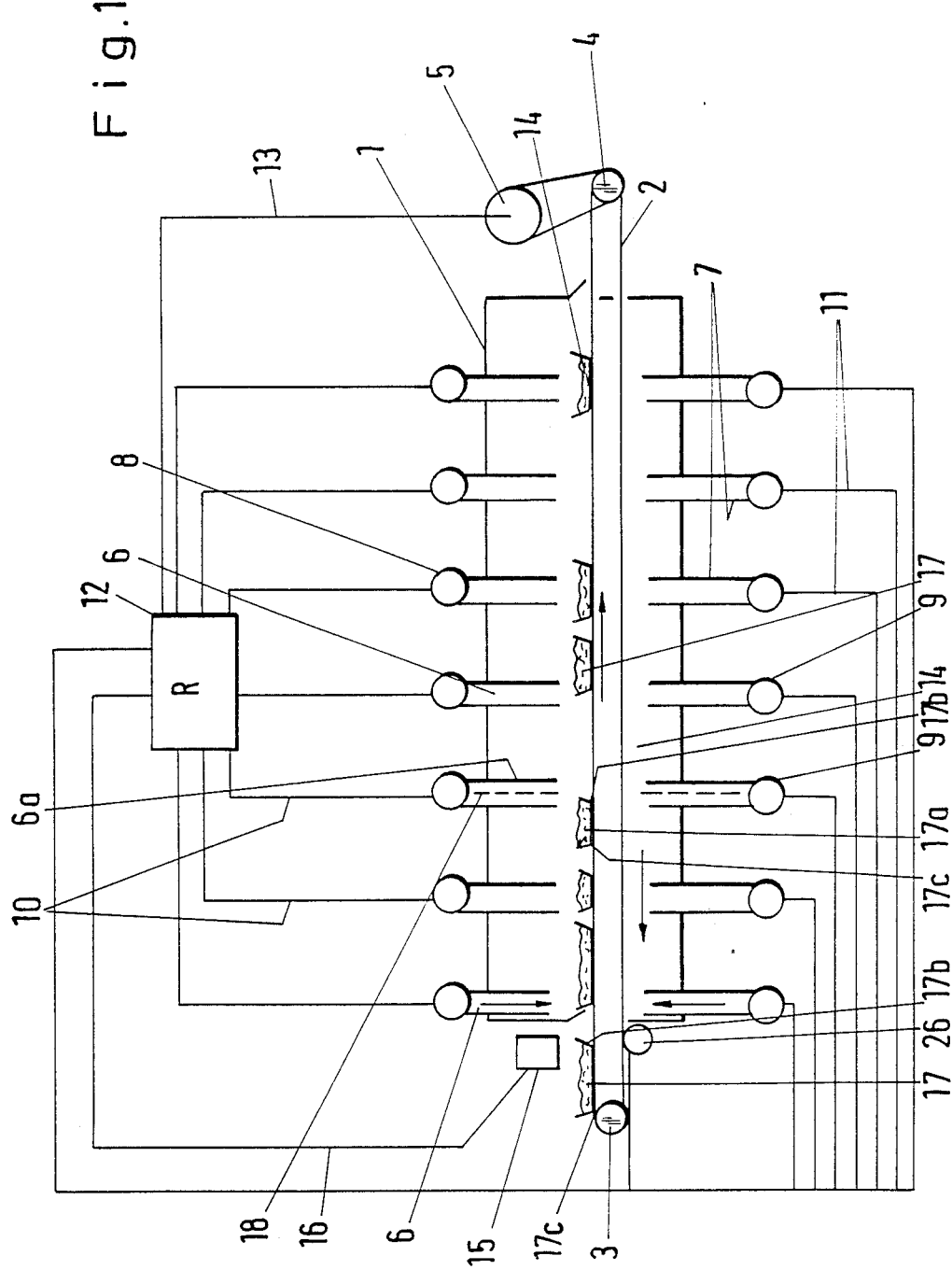
FIG. 1. shows a diagrammatic longitudinal section through, the microwave system of the present invention.

A continuous conveyor belt 2 is led through the treatment chamber 1 and guided around the guide rollers 3 and 4. A drive 5 is connected to the guide roller 4, and by line 13 to computer 12.

Extending into the treatment chamber are upper microwave input channels 6 and lower microwave input channels 7, to which in each case upper generators 8 and lower generators 9 are connected for generating the microwave energy. In FIG. 1, the channels 6 and 7 are vertically aligned, while in FIG. 2 the channels are shown longitudinally off-set.

The upper generators 8 are connected by means of the lines 10, and the lower generators 9 are connected by means of the lines 11 to a computer 12.

For the purpose of registering the exact positions of the containers 17 on the conveyor belt 2, a reflection light barrier 15 is provided which is connected by means of the line 16 to the computer 12 and to a generally known motion pickup 26. Although the reflection light barrier is shown and preferred, other devices for indicating the presence of a container are mechanical sensors, optical sensors, laser beam sensors, dynamic pressure air jets, proximity switches, or ultra-sound or infrared sensors.

The method of functioning of the microwave system is as follows. The position of the package 17a on the conveyor belt 3, that is especially the beginning 17b and the end 17c, is recorded by the registering device 15 and transmitted to the computer 12.

The registering device is in this case a reflection light barrier 15, which works in conjunction with a motion pickup 26 connected to the computer 12. The motion pickup 26 converts the belt movement into electrical pulses, which can be dimensioned such that one impulse is transmitted to the computer per millimeter of belt movement, for example. With this resolution, the switching points for switching the microwave energy on and off can be defined to the millimeter precisely in relation to the container length and the aperture center of the input channel.

In the course of the exact registration of the beginning 17b and the end 17c, the computer 12 calculates the switch-on and switch-off points of the microwave energy in relation to the container position on the belt.

When the package 17a runs through with its switch-on point 23 under the aperture center of the input channel 18, the computer 12 switches the microwave energy on. The switching on of microwave energy is on the basis of the calculation of the path traveled by the package 17 with the conveyor belt 3 up to beneath the aperture center 18 of the input channel 6a.

After passing the switch-off point 24 under the aperture center 18, the microwave output from channel 6a is switched off by the computer 12, before the end of the container is reached.

This operation is carried out without it being necessary to sense the beginning 17b or end 17c of the package in the chamber 1. The computer calculates in each case the exact time of the beginning and of the end of the microwave output for each individual channel 6, 7 and for each individual package solely by registering the position of the package 17 on the conveyor belt 3 before entering into the treatment chamber. The immovable arrangement of the input channels 6 and the distances 25 between them is likewise taken into account by the computer 12 when the packages 17 run through the treatment chamber 1.

Each generator 8 and 9 connected to an input channel 6 or 7 is controlled regarding its energy as well as its switch-on time by the computer 12. Control takes place on the basis of the registration by the reflection light barrier 15 regardless of the speed of the conveyor belt 3, or in accordance with input of the parameters for the package length, package contents, weight and density of the product to be treated, the dielectric values of the product and the required temperature increase delta-T.

It should be emphasized that the microwave coupling of the generators 8 and 9 is controlled by the computer 12 for each individual input channel 6, 7 and for each individual package on the basis of the above parameters. It is of no consequence whether the packages lie on the conveyor belt 3 at an exact distance from one another. Each package is registered individually and the microwave input cycle length of the generators is controlled for each package in each case. It is of no significance whether long or short packages with a small or large distance between are laid alternately on the conveyor belt.

The contents of a container can comprise, for example, three different food products in the conveying direction, such as rice, meat with gravy, and vegetables, but the products are heated evenly due to the setting of the switch-on and switch-off points of the microwave input associated with the product limits, although the individual components have different densities, weights and dielectric values.

FIG. 2 shows in diagrammatic fashion a preferred example of a method of operation which leads to even more economic operation and an extremely even heating of the packages and the package edges.

The container 17a on the conveyor belt 2 is led in the direction of arrow 19 through the treatment chamber (not shown here).

The container 17a first runs under the input channel 6a. The switch-on point 23 of the input microwave energy is set in relation to the container length and to the axial aperture center 18 of the input channel 6a and is dependent on the product to be pasteurized in the container.

The path distance which the container has traveled until the energy input is switched on is denoted by 20. The path distance which is equivalent to the switch-on time or the cycle time of the microwave input as a function of the belt speed, is denoted by 21. The distance 22 represents the path traveled by the container on the conveyor belt 2 in order to move out of the range of the input channels 6 and 7.

The switch-off point of the microwave input is denoted by 24. The switch-on operation is initiated in this case when the switch-on point under/over the aperture center 18 of the input channels is passed. This state is represented by the lower input channel 7b. The switch-off point 24 is behind the aperture center 18 of the lower input channel 7b. Depending on the product to be treated, the switch-on point 23 and the switch-off point 24, that is the switch-on path (cycle length), can be selected differently.

If less microwave treatment is expedient, the path distances 20 and 22 are extended, as a result of which the cycle time 21, that is the treatment duration, is shortened. The cycle length 21 is selected according to the length of the container 17. The respective length of the path distances 20 or 22 is important for a better temperature distribution in the containers.

It may be expedient with container contents, for example, a ready meal with a relatively large proportion of gravy (water portion), to make the switch-on point 23 coincide with the beginning 17b of the container and to make the switch-off point 24 coincide with the end 17c of the container.

The switch-on and switch-off points 23, 24 are selected in each individual case depending on the product to be treated and the container length in each case, and is always related to the aperture center 18 of the input channels.

The microwave input is controlled, as described above, on the basis of the registration of the position of the container 17 on the conveyor belt 2, to be precise before entry into the treatment chamber 1. As a result of a corresponding programming of the computer 12, taking into account the speed of the conveyor belt 1, the container length, the desired cycle time 21 and the energy amount, the energy output of each individual input channel 6 and 7 is controlled. In this arrangement the computer 12 can also be divided up into individual microprocessors assigned to the magnetrons and a master processor.

By virtue of this method and the apparatus used for implementing the method, for the first time an even heating of homogeneously filled container contents (for example, pasta with sauce) is ensured because the cycle time 21 is selectable, an even heating of a container filled with three different products (rice, meat with gravy, vegetables) is ensured, containers of different lengths with arbitrary distances between them can be placed on the conveyor belt, it is ensured that the system permits the highest possible utilization of expensive microwave energy because, as a result of the computer control, the cycle time, the container length, and the belt speed can be taken into account specifically and each input channel can be controlled separately.

If the microwave input between the switch-on and switch-off points is intermittent, a further improvement of the temperature evenness is obtained.

Figures 4, 5, 6:
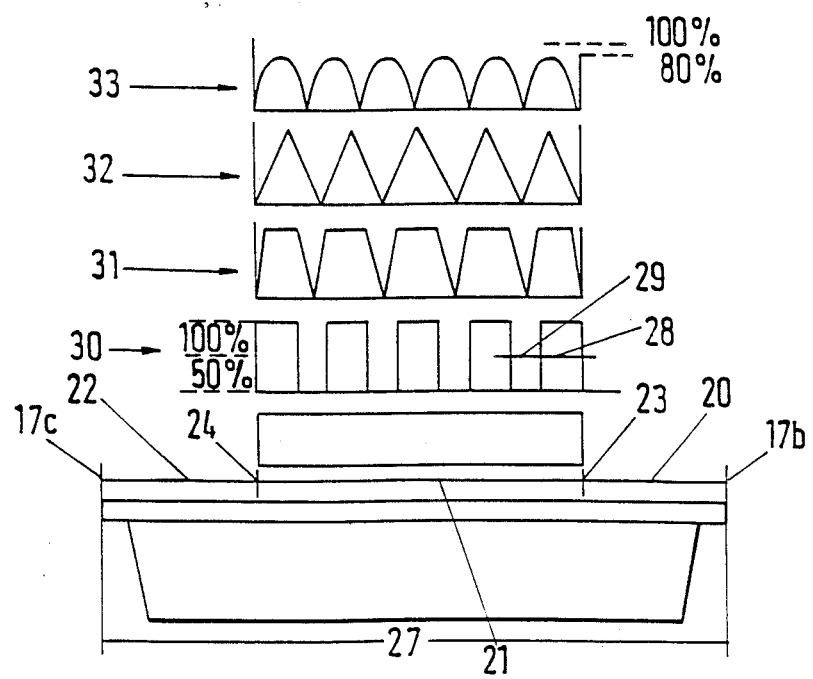
FIG. 4 shows a representation of the temperature distribution according to the prior art with a microwave input without control of the individual generators.
FIG. 5 shows a representation of the temperature distribution with a synchronization during the microwave input operation of the individual generators in accordance with the invention.
FIG. 6 shows a representation of the various forms and levels of microwave energy, also in connection with a synchronization during the input operation of the individual generators in accordance with the invention.

With a cycle length of, for example, 4 s and a pulse of likewise 4 s, the product center tying approximately 20° C. lower in comparison to the edge zones in the case of conventional continuous energy according to the prior art can be raised to the same temperature as the edge zones (FIG. 5).

Referring to the results illustrated in FIGS. 4 and 5, the application of the method of operation described (pulsed microwave energy) makes it possible to achieve a homogenous temperature field in the treated goods even with a slow conveying speed. FIG. 4 represents temperature variations in prior art arrangements, and FIG. 5 represents the even temperature achieved in accordance with the present invention.

A further positive effect has emerged, in that in the case of sealed plastics packages the inflation of the sealing foil as a result of inner excess pressure becomes negligibly small. During the energy cycle, the head area expansion begins after several seconds, and becomes critically large after approximately 5 s. As a result of the equally long input pause, this inflation disappears again and begins again at 0 at the next energy pulse.

Together with switching on and switching off this pulse operation as defined by the package length, an even heating of the product is thus ensured.

Moreover, as a result of the intermittent input of energy between the switch-on and switch-off points 23 and 24, in contrast to a continuous operation according to the prior art, the penetration speed of the microwave energy into the product is significantly increased so that the product surface is less overheated.

FIG. 6 illustrates the form of the microwave energy which is input between the switch-on point 23 and the switch-off point 24 through the input channels 6, 7 into the container 17.

The form of the energy influences the temperature of the product surface. As the product surface temperature increases, the energy peak should act more briefly on the product surface. The rectangular energy form 30 has the greatest influence on the product surface. The trapezoidal energy form 31 reduces this influence, and the triangular energy form 32 leads to a further reduction of the influence on the product surface.

If, in addition to selecting a sinusoidal energy form 33, the energy level is also reduced from 100% to 80%, very good results are obtained.

As a result of a pulsing operation of the system, that is a pulsed input of the microwave energy (between the switch-on and switch-off points 23, 24), it was surprisingly found that sealed packages no longer burst even when product temperatures reach 85–95° C., which represents a considerable technical advance.

Example

There is placed into the food package made of, for example, a deep-drawn and sealed plastics foil a preprepared lasagna dish which is to be subjected to a pasteurization operation in order to destroy bacteria to prolong the time in which it can be consumed or the time it stays fresh.

The packages have the following dimensions:
Length: 190 mm
Width: 140 mm
Height: 28 mm
Weight: 400 g In order to obtain the desired product temperature of 80° C. for the pasteurizing operation, an energy requirement of 0.025 kWh per 400 g package is calculated for the run-through time, assuming identical package dimensions and a product input temperature of 40° C.

The computer 12 is programmed as follows:
(a) all upper generators 8 and lower generators 9 are programmed for an energy output of 1.2 kW each, so that altogether each lasagna package is subjected to a total of 1.2 kW microwave energy from above and from below in each case through the input channels 6 and 7 during the cycle time 21.
(b) There are seven upper and seven lower input channels 6 and 7. The total microwave treatment time of approximately one minute is divided into 8.5 seconds per upper and lower input aperture, that is, the cycle time 21 of the lasagna package is 8.5 seconds from the switch-on point 23 to the switch-off point 24.

A total energy treatment time of 7 × 8.5 seconds = approx. 1 minute is thus realized at a constant microwave energy output of 1.2 kW, specifically in each case with the fill required energy of 1.2 kW per magnetron and per package.

The distance from the exit aperture of the input channels 6 and 7 to the product surface is 50 mm.

A microwave system using a wavelength of 12 cm or 120 mm (frequency of 2,450 GHz) is used.

A typical temperature distribution in the package is shown in FIG. 3, and the evenness will be noted.

It is clear from FIG. 3 that the temperature difference in the package, especially with respect to the edge regions compared to the center, is only very slight, so that a burning of the edge regions is avoided. A very uniform destruction of bacteria over the entire surface was observed.

What is claimed is:

1. A method for the even heating of food products in containers, the containers traveling longitudinally on a continuous conveyor through a microwave treatment chamber, the heating being effected by longitudinally spaced microwave input channels positioned above and/or below said conveyor and extending into said treatment chamber, said channels having axial aperture centers and being operatively connected to microwave generators, comprising the steps of:
   (a) registering before or during initial entry into the treatment chamber at least the beginning and end of each container positioned on said conveyor, without regard to the spacing between said containers, and transmitting such position information to a computer,
   (b) switching on each microwave generator when a predetermined switch-on point of said container passes the axial aperture center of the associated input channel,
   (c) switching off each microwave generator when a predetermined switch-off point of said container passes said axial aperture center of said associated input channel, and
   (d) determining said switch-on and switch-off points based on the container length, the product to be heated, and the position of the axial aperture center, all of which are set or preset in the computer.

2. The method of claim 1, characterized in that the beginning and end of each container is input directly into the computer as a fixed length dimension between said beginning and end.

3. The method of claim 1, characterized in that the input microwave energy of each individual input channel is switched on at the time or after the beginning of the container passes under or over the axial aperture center of the input channels, and is switched off before or at the time the end pass by.

4. The method of claim 1, characterized in that the input microwave energy is preset in the computer depending on the product to be treated and the speed of the conveyor belt, the weight and density of the container contents, the dielectric values of the product to be treated, and the required temperature increase in the product during the microwave treatment.

5. The method of claim 1, characterized in that the microwave energy emitted through the input channels by the microwave generators between the switch-on point and the switch-off point is input intermittently into the containers, at a variably selected level and form.

6. An apparatus for the heating of food products in containers, the containers travelling longitudinally on a continuous conveyor through a microwave treatment chamber, comprising,
   (a) microwave input channels spaced longitudinally in said treatment chamber above and/or below said conveyor and said containers supported thereby, and microwave generators associated with said input channels and with a computer for controlling said generators and consequently said microwave input channels, said input channels having axial aperture centers,
   (b) registering means positioned exteriorly of said treatment chamber for registering the beginning and the end of a container positioned on said conveyor prior to passage through said treatment chamber, such information being transmitted to said computer, and
   (c) said computer computing longitudinally spaced switch-on and switch-off points between which microwave energy is switched on and outside of which microwave energy is switched off,
   said computer determining said switch-on and switch-off points based on the container length, the weight, density and dielectric values of the product, and the required temperature increase.

7. The apparatus according to claim 6, wherein said registering means comprises a reflection light barrier which interacts with a motion pickup to transmit the positions of the containers on the conveyor belt to the computer for the switch-on and switch-off operation of the individual generators.

8. The apparatus of claim 6, wherein said registering device may be a mechanical sensor, optical sensor, laser beam sensor, dynamic pressure air jet, proximity switch, ultrasound sensor or infrared sensor.

9. The apparatus of claim 6, wherein input channels project vertically from both above and below the conveyor into the treatment chamber, said channels positioned above being arranged in series in the work direction alternately with the input channels projecting vertically from below into the chamber.

10. The apparatus of claim 6, wherein input channels project vertically from both above and below the conveyor into the treatment chamber, said channels positioned above being arranged opposite said input channel positioned below.

* * * * *